(12) United States Patent
Eguchi

(10) Patent No.: US 7,105,846 B2
(45) Date of Patent: Sep. 12, 2006

(54) RADIOACTIVE SAMPLE HOLDER

(75) Inventor: Kenzo Eguchi, Machida (JP)

(73) Assignee: Anzai Medical Kabushiki Kaisha, Tokyo (JP)

(*) Notice: Subject to any disclaimer, the term of this patent is extended or adjusted under 35 U.S.C. 154(b) by 0 days.

(21) Appl. No.: 11/123,781

(22) Filed: May 6, 2005

(65) Prior Publication Data

US 2006/0091329 A1     May 4, 2006

(30) Foreign Application Priority Data

Nov. 1, 2004 (JP) ............................. 2004-317893
Feb. 18, 2005 (JP) ............................. 2005-042387

(51) Int. Cl.
*G21F 5/018* (2006.01)
*A61B 6/10* (2006.01)

(52) U.S. Cl. ............................. 250/506.1; 250/496.1; 250/522.1

(58) Field of Classification Search ..................... None
See application file for complete search history.

(56) References Cited

U.S. PATENT DOCUMENTS 5,099,129 A * 3/1992 Pullan ..................... 250/385.1

FOREIGN PATENT DOCUMENTS

JP     01-244759     9/1989

OTHER PUBLICATIONS

"CURIEMETER IGC-7" issued by ALOKA CO., LTD. (Sep. 2000).

* cited by examiner

*Primary Examiner*—Nikita Wells
(74) *Attorney, Agent, or Firm*—Paul A. Guss

(57) ABSTRACT

After a syringe containing a radioactive sample therein and housed in a radiation shield case is mounted on a radioactive sample holder and set in a radioactive sample measuring apparatus, an upwardly projecting handle of the radioactive sample holder is depressed to cause a syringe holder base supported on second shafts to lower a flange of the syringe held by the syringe holder base, pulling the syringe out of the radiation shield case. Then, the amount of radioactivity of the radioactive sample contained in the syringe is measured.

8 Claims, 16 Drawing Sheets

RADIOACTIVE SAMPLE HOLDER

BACKGROUND OF THE INVENTION

1. Field of the Invention

The present invention relates to a radioactive sample holder for holding a syringe containing a radioactive sample, the radioactive sample holder being adapted to be loaded into a radioactivity measuring apparatus for measuring an amount of radioactivity of the radioactive sample.

2. Description of the Related Art

There have been developed a method of and an apparatus for measuring a level of radiation emitted from a radioactive sample that is administered to an examinee and which concentrates on a certain body region of the examinee, thereby inspecting the state of the examinee.

The radioactive sample is usually introduced from a radioactive sample dispenser (see Japanese Patent Publication No. 3-31468) into a syringe, and then administered from the syringe to the examinee. For accurately inspecting the state of the examinee, it is necessary to supply the syringe with a sufficient amount of radioactive sample. A radioactivity measuring apparatus disclosed in a catalog entitled "CURIEMETER IGC-7" (issued by ALOKA CO., LTD. in September, 2000) has been developed for measuring an amount of radioactivity of the radioactive sample held in the syringe.

The disclosed radioactivity measuring apparatus utilizes an ionizing action of radiation emitted from the radioactive sample. As shown in FIG. 16 of the accompanying drawings, a syringe 2 containing a radioactive sample therein is held by a holder 4, which is inserted into a hollow cylindrical detector 6 having a built-in sensor for measuring a level of radiation emitted from the radioactive sample.

The holder 4 has an engaging arm 8 disposed on its upper end for engaging an upper open end of the detector 6. The holder 4 also has a holder ring 12 for holding the syringe 2, the holder ring 12 being mounted on the lower end of a shaft 10 extending vertically downwardly from the engaging arm 8. The syringe 2 has a hollow cylinder 14 including a flange 16 on its upper end and a needle 18 extending downwardly from the lower end of the hollow cylinder 14. The syringe 2 is held by the holder ring 12 with the flange 16 resting on an upper surface of the holder ring 12 and the needle 18 extending downwardly.

When the syringe 2 is held by the holder ring 12 with the needle 18 extending downwardly, the radioactive sample contained in the syringe 2 may possibly leak out through the needle 18. Usually, a plurality of syringes 2 of different sizes containing respective different amounts of the radioactive sample are provided for use with the radioactivity measuring apparatus. In order to hold the different syringes 2, the radioactivity measuring apparatus must have a plurality of holders 4 having respective holder rings 12 with different sizes matching the sizes of each of the syringes 2. In addition, as shown in FIG. 16, when the exposed syringe 2 is to be inserted into the detector 6, the operator needs to exercise adequate care in handling the syringe 2 to avoid exposure to the radioactive sample contained in the syringe 2.

SUMMARY OF THE INVENTION

It is a general object of the present invention to provide a radioactive sample holder which is capable of stably holding a syringe containing a radioactive sample and which is compatible with various syringes having different sizes.

Another object of the present invention is to provide a radioactive sample holder which can be loaded into a radioactivity measuring apparatus without the danger of leakage of radiation from a radioactive sample.

Still another object of the present invention is to provide a radioactive sample holder which holds a syringe containing a radioactive sample without the danger of leakage of radiation from the radioactive sample.

Yet another object of the present invention is to provide a radioactive sample holder which can be loaded into a radioactivity measuring apparatus to allow the radioactivity measuring apparatus to highly accurately measure an amount of radioactivity of a radioactive sample that is contained in a syringe.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
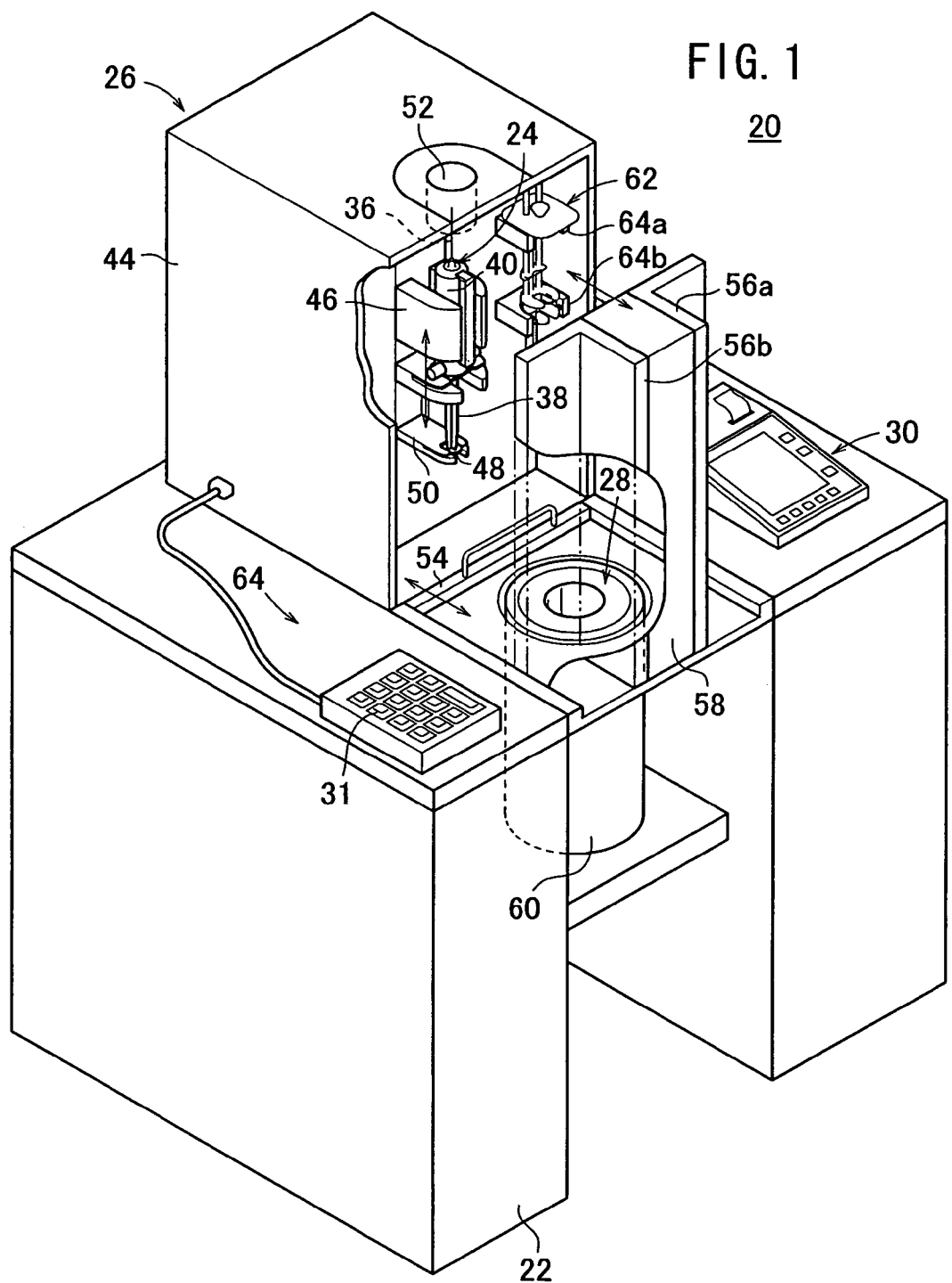
FIG. 1 is a perspective view, partly broken away, of a radioactive sample introducing and measuring system which incorporates a radioactive sample holder according to a first embodiment of the present invention.

FIG. 1 shows in perspective, partly broken away, a radioactive sample introducing and measuring system 20 which incorporates a radioactive sample holder 62 according to a first embodiment of the present invention.

As shown in FIG. 1, the radioactive sample introducing and measuring system 20 comprises a radioactive sample introducing apparatus 26, which is mounted on a worktable 22, for introducing a predetermined amount of radioactive sample into a syringe 24, a radioactive sample measuring apparatus 28 disposed substantially centrally in the worktable 22 for measuring an amount of radioactivity of the radioactive sample contained in the syringe 24, and a measurement display unit 30 for controlling the radioactive sample measuring apparatus 28 to measure and display an amount of radioactivity of the radioactive sample. The radioactive sample introducing apparatus 26 is controlled by a controller 31.

Figure 2:
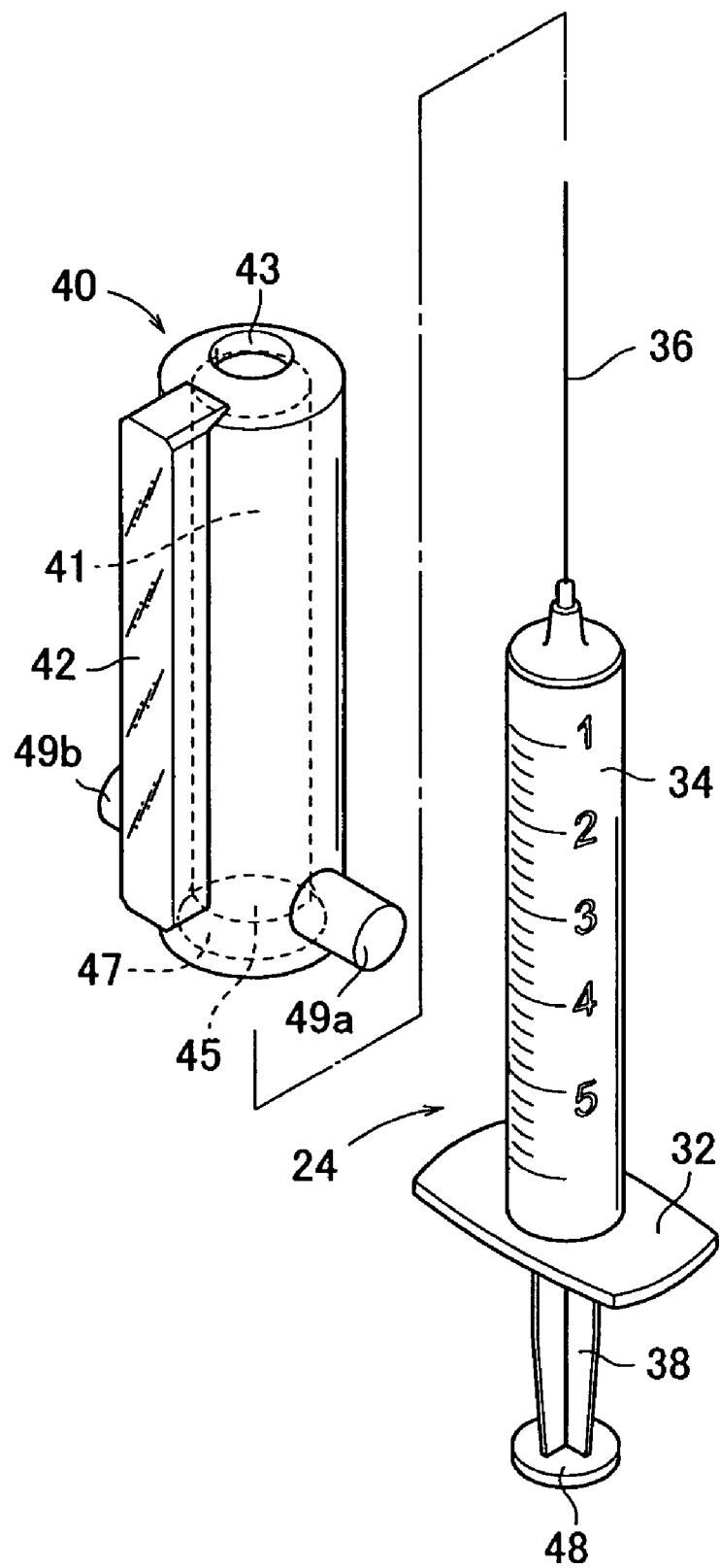
FIG. 2 is a perspective view of a syringe and a radiation shield case which are held by the radioactive sample holder according to the first embodiment.

As shown in FIG. 2, the syringe 24 comprises a hollow cylinder 34 having a flange 32 on an end thereof, a needle 36 mounted on the opposite end of the cylinder 34, and a piston 38 telescopically inserted in the cylinder 34 through the flanged end thereof. The syringe 24 is housed in a hollow cylindrical radiation shield case 40 that is made of lead, tungsten, or the like.

The radiation shield case 40 has an insertion cavity 41 for inserting the cylinder 34 of the syringe 24 therein. The radiation shield case 40 also has an upper opening 43 defined in an upper end thereof above the insertion cavity 41 for allowing the needle 36 mounted on the cylinder 34 that is inserted in the insertion cavity 41 to extend therethrough out of the radiation shield case 40, and a lower opening 45 defined in a lower end thereof beneath the insertion cavity 41 for allowing the cylinder 34 to be inserted therethrough into the insertion cavity 41, with the flange 32 and the piston 38 being disposed out of the radiation shield case 40. The annular edge of the radiation shield case 40 that surrounds the lower opening 45 has an annular tapered surface 47 for allowing the cylinder 34 to be inserted easily into the radiation shield case 40. A vertically elongate lead glass plate 42 is axially mounted on an outer circumferential surface of the radiation shield case 40 for making the amount of radioactive sample contained in the cylinder 34 that is inserted in the insertion cavity 41, visible from outside of the radiation shield case 40. A pair of diametrically opposite arms 49a, 49b is mounted on and projects laterally from the outer circumferential surface of the radiation shield case 40 near its lower end for holding the radiation shield case 40 on the radioactive sample holder 62 to be described later.

The radioactive sample introducing apparatus 26 has a column 44 supporting on its front surface a retainer 46 for retaining the radiation shield case 40 with the syringe 24 housed therein, and an engaging tongue 50 engageable with a flange 48 of the piston 38 of the syringe 24. The retainer 46 and the engaging tongue 50 are vertically movable. A sample container 52 containing a radioactive sample therein is loaded in the column 44 above the retainer 46.

Figure 3:
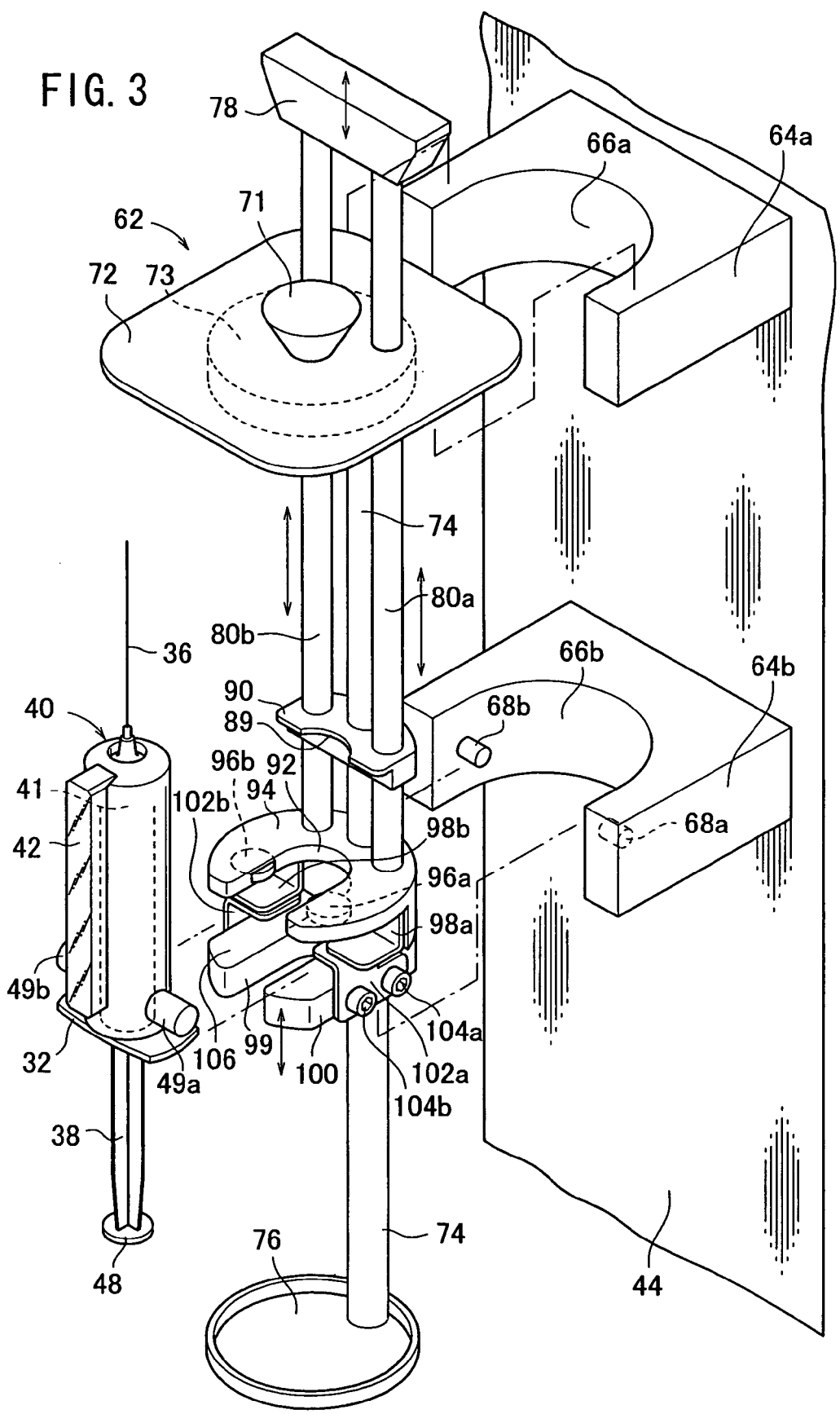
FIG. 3 is an exploded perspective view of the radioactive sample holder according to the first embodiment and mounts for mounting the radioactive sample holder thereon.
Figure 4:
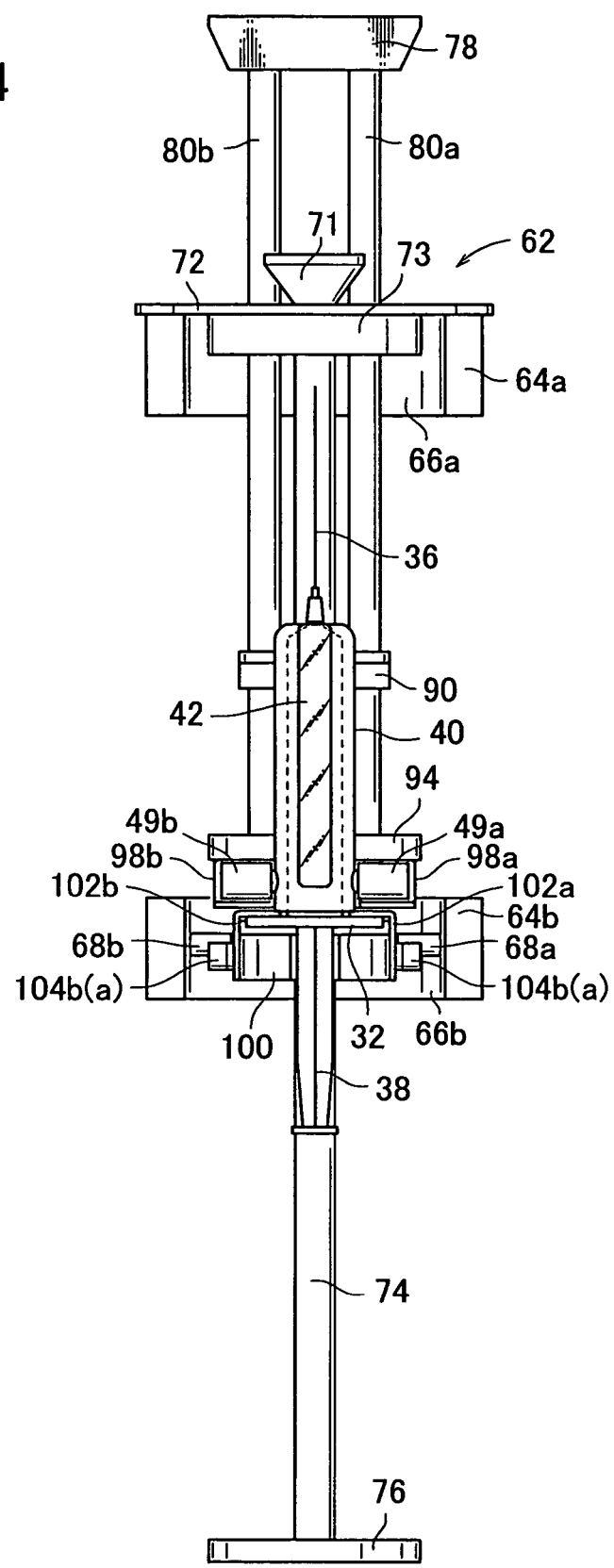
FIG. 4 is a front elevational view showing the syringe which is held by the radioactive sample holder according to the first embodiment through the mounts.
Figure 5:
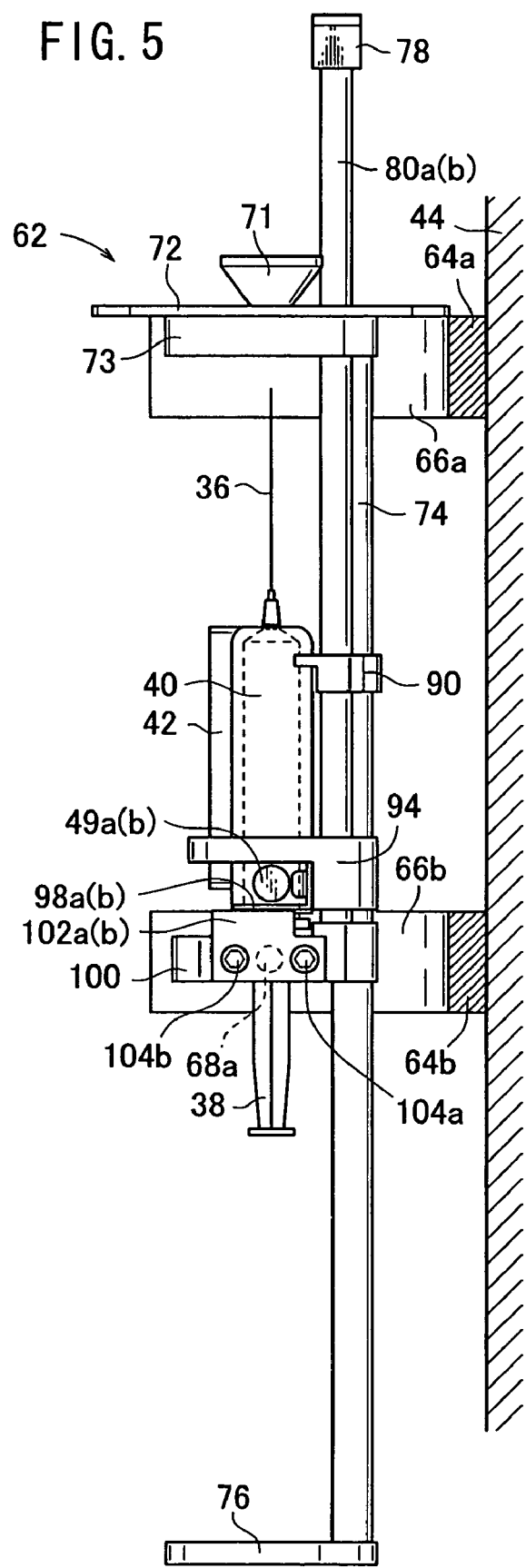
FIG. 5 is a side elevational view showing the syringe which is held by the radioactive sample holder according to the first embodiment through the mounts.

The column 44 also supports on its front surface a pair of vertically spaced mounts 64a, 64b disposed laterally of the retainer 46 for temporarily mounting the radioactive sample holder 62 for holding the syringe 24 and the radiation shield case 40. As shown in FIG. 3, the vertically spaced mounts 64a, 64b have respective semicircular engaging surfaces 66a, 66b for engaging the radioactive sample holder 62. A pair of engaging pins 68a, 68b for engaging a portion of the radioactive sample holder 62 is embedded in the lower engaging surface 66b.

A lead shield plate 54, which is movable between a position above the radioactive sample measuring apparatus 28 and the radioactive sample introducing apparatus 26, is disposed in the lower end of the column 44. A lead glass plate 58 for blocking radiation from the radioactive sample introducing apparatus 26 is disposed in front of the radioactive sample introducing apparatus 26 and has opposite sides held by a pair of L-shaped metal plates 56a, 56b containing lead. The lead glass plate 58 is movable toward and away from the radioactive sample introducing apparatus 26.

The radioactive sample measuring apparatus 28 is disposed between the lead glass plate 58, which is displaced away from the radioactive sample introducing apparatus 26, and the radioactive sample introducing apparatus 26. The radioactive sample measuring apparatus 28 comprises a hollow cylindrical body 60 having a radioactive sensor (not shown) housed in the worktable 22. The radioactive sample holder 62 holding the syringe 24 and the radiation shield case 40 is inserted in the hollow cylindrical body 60.

Figure 6:
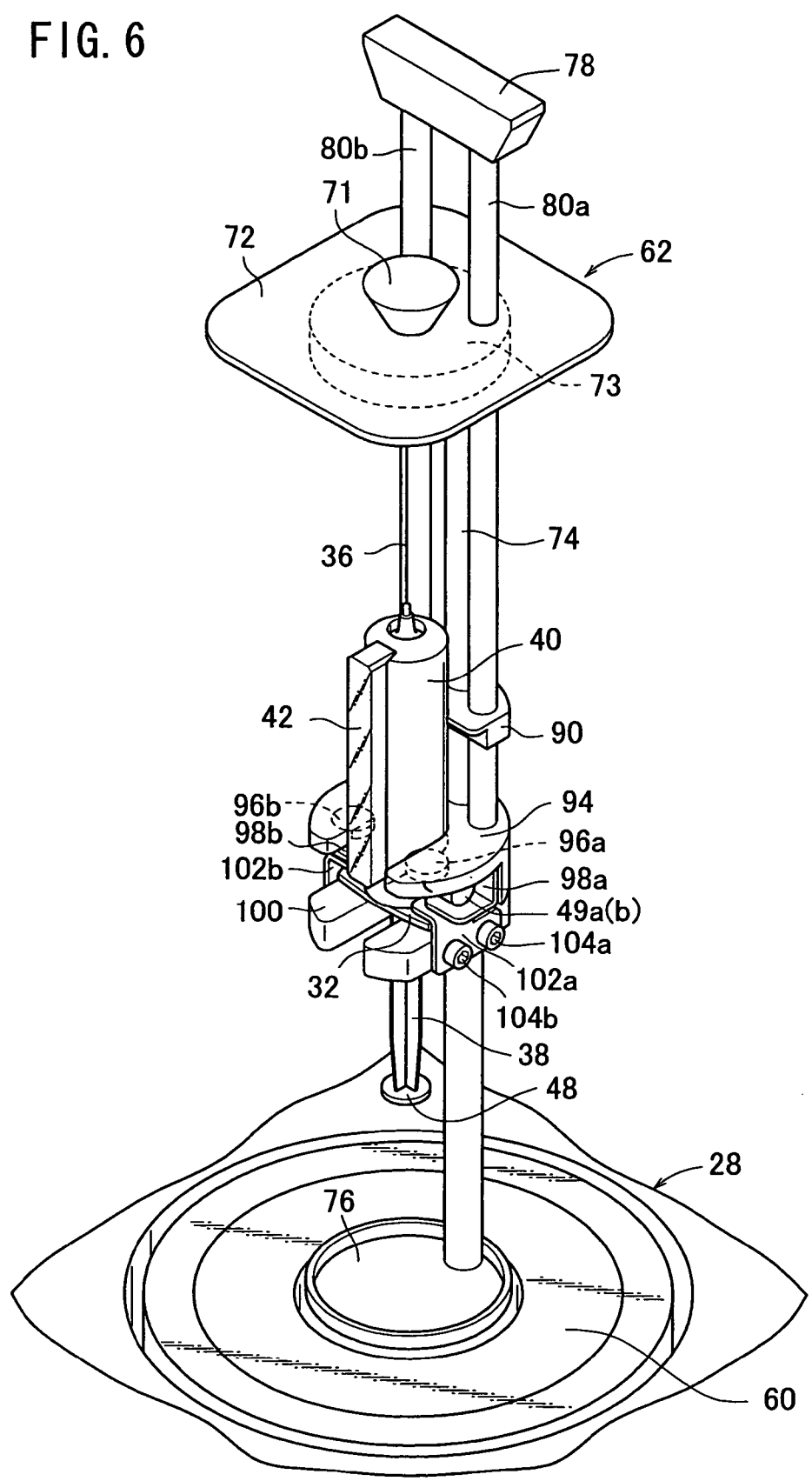
FIG. 6 is a perspective view showing the manner in which the radioactive sample holder according to the first embodiment with the syringe held thereby is inserted into a radioactivity measuring apparatus.

As shown in FIGS. 3 through 6, the radioactive sample holder 62 comprises a radiation shield plate 72 made of a radiation shielding material such as tungsten or the like and having a knob 71 on its upper surface, a circular guide plate 73 mounted on a lower surface of the radiation shield plate 72 and having a diameter substantially equal to the inside diameter of the hollow cylindrical body 60 of the radioactive sample measuring apparatus 28, a first shaft 74 extending vertically downwardly from the radiation shield plate 72, and a circular guide plate 76 mounted on the lower end of the first shaft 74 and having a diameter slightly smaller than the inside diameter of the hollow cylindrical body 60 (see FIG. 6).

Figure 7:
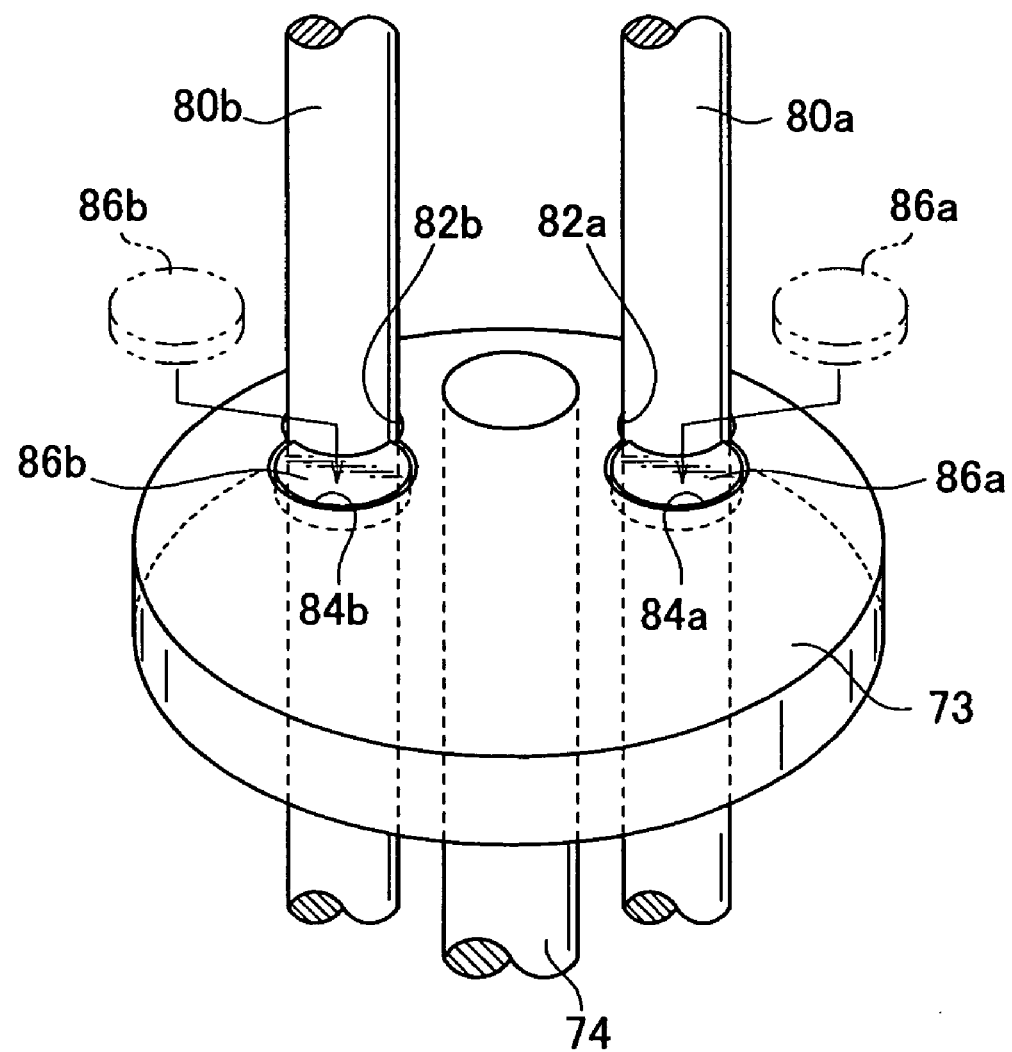
FIG. 7 is a perspective view of shafts and a guide plate in a frictional sliding region of the radioactive sample holder according to the first embodiment.

The radioactive sample holder 62 also has a handle 78 on its upper end and a pair of second shafts 80a, 80b vertically displaceable extending from the handle 78 downwardly through the radiation shield plate 72 and the guide plate 73. As shown in FIG. 7, the guide plate 73 has a pair of spaced holes 82a, 82b through which the second shafts 80a, 80b extend, respectively, and also has a pair of spaced holes 84a, 84b communicating with portions of the holes 82a, 82b, respectively. Circular resistive members 86a, 86b made of silicone rubber or the like are inserted into the respective holes 84a, 84b. The circular resistive members 86a, 86b are elastically deformed with their outer circumferential surfaces held partly in frictional contact with the outer circumferential surfaces of the second shafts 80a, 80b, respectively, imparting frictional resistance to the second shafts 80a, 80b. Therefore, the syringe 24 held by the radioactive sample holder 62 is prevented from dropping by gravitational force, and vertical displacement of the second shafts 80a, 80b is optimized. According to a modification shown in FIG. 8, the holes 82a, 82b may have an inner diameter slightly greater than the outer diameter of the second shafts 80a, 80b, and resistive members 88a, 88b may be inserted between the inner surfaces of the holes 82a, 82b and the resistive members 88a, 88b for imparting frictional resistance to the second shafts 80a, 80b.

A first retainer 90 is fixed to a substantially central portion of the first shaft 74. The first retainer 90 has a forwardly open recess 89 defined in its front edge for abutting engagement with an upper outer circumferential surface of the radiation shield case 40 with the syringe 24 housed therein. A second retainer 94 is also fixed to a portion of the first shaft 74 beneath the first retainer 90. The second retainer 94 has a forwardly open U-shaped groove 92 defined in its front edge for inserting therein a lower outer circumferential surface of the radiation shield case 40. The second retainer 94 has a pair of elastic members 96a, 96b made of silicone rubber or the like which are embedded as resistive members therein and have portions projecting into the U-shaped groove 92 from its opposite side edges for frictional contact with the outer circumferential surface of the radiation shield case 40 to prevent the radiation shield case 40 with the syringe 24 housed therein from dropping off the radioactive sample holder 62. A pair of third retainers 98a, 98b for holding the respective arms 49a, 49b mounted on the outer circumferential surface of the radiation shield case 40 near its lower end is fixed to a lower portion of the second retainer 94.

The second shafts 80a, 80b extend downwardly through the first retainer 90 and the second retainer 94 which are fixed to the first shaft 74. A syringe holder base 100 for holding the lower surface of the flange 32 of the syringe 24 housed in the radiation shield case 40 is fixed to the lower ends of the second shafts 80a, 80b. The syringe holder base 100 has a U-shaped groove 99 for inserting therein the piston 38 of the syringe 24. A pair of brackets 102a, 102b for holding the upper surface of the flange 32 of the syringe 24 is fixed to the syringe holder base 100. The brackets 102a, 102b have upper shoulders spaced upwardly from the upper surface of the syringe holder base 100 by a distance corresponding to the thickness of the flange 32. The syringe holder base 100 has a front step 106 projecting a predetermined distance forwardly from the second retainer 94 that is positioned above the syringe holder base 100. The brackets 102a, 102b are fixed to respective side edges of the syringe holder base 100 by screws 104a, 102b.

The radioactive sample introducing and measuring system 20 which incorporates the radioactive sample holder 62 according to the first embodiment is basically constructed as described above. A process of introducing and measuring a radioactive sample using the radioactive sample introducing and measuring system 20 will be described below.

First, the operator inserts the syringe 24 into the radiation shield case 40 through its lower opening 45, and thereafter retains the radiation shield case 40 on the retainer 46 of the radioactive sample introducing apparatus 26, with the flange 48 of the piston 38 engaged by the engaging tongue 50. Then, the operator moves the lead glass plate 58 to the radioactive sample introducing apparatus 26, providing a radiation shielding environment in the radioactive sample introducing apparatus 26. Then, the operator operates the controller 31 to start introducing a radioactive sample into the syringe 24.

The retainer 46 and the engaging tongue 50, which retains the syringe 24, are elevated to insert the needle 36 into the sample container 52 that is positioned above the retainer 46. Then, the engaging tongue 50 is lowered a distance commensurate with the amount of radioactive sample which has been indicated by the controller 31, drawing the indicated amount of radioactive sample from the sample container 52 through the needle 36 into the cylinder 34.

After the radioactive sample is introduced into the syringe 24, the operator displaces the lead glass plate 58 away from the radioactive sample introducing apparatus 26, and then removes the radiation shield case 40 with the syringe 24 mounted therein from the retainer 46. The operator then places the radiation shield case 40 with the syringe 24 mounted therein on the radioactive sample holder 62 mounted on the mounts 64a, 64b.

At this time, the radioactive sample holder 62 is in such an operative position that the handle 78 is lifted to its uppermost position, the radiation shield plate 72 is mounted on the upper surface of the mount 64a, and the second retainer 94 and the syringe holder base 100 are held in engagement with the engaging surface 66b of the mount 64b. The engaging pins 68a, 68b embedded in the lower engaging surface 66b are positioned between the screws 104a, 104b by which the brackets 102a, 102b are fastened to the syringe holder base 100, preventing the radioactive sample holder 62 from being easily dislodged from the mounts 64a, 64b (see FIG. 5).

Then, the operator places the radiation shield case 40 with the syringe 24 mounted therein onto the radioactive sample holder 62 with the needle 36 pointing upwardly.

Specifically, the operator inserts the lower portion of the radiation shield case 40 into the U-shaped groove 92 in the second retainer 94, and brings the upper portion of the radiation shield case 40 into the recess 89 in the first retainer 90. At this time, the lower outer circumferential surface of the radiation shield case 40 is reliably held by the elastic members 96a, 96b projecting into the U-shaped groove 92. The arms 49a, 49b on the lower portion of the radiation shield case 40 are engaged and retained by the third retainers 98a, 98b that are disposed below the second retainer 94. The flange 32 of the syringe 24 mounted in the radiation shield case 40 is inserted over the step 106 of the syringe holder base 100 into a position between the syringe holder base 100 and the brackets 102a, 102b, and held in that position (see FIGS. 3 and 4). Since the radioactive sample holder 62 holds the syringe 24 with the flange 32 of the cylinder 34 being inserted between the syringe holder base 100 and the brackets 102a, 102b, the radioactive sample holder 62 is able to hold various syringes 24 of different sizes insofar as their pistons 38 have diameters small enough to be inserted into the U-shaped groove 99.

Figure 8:
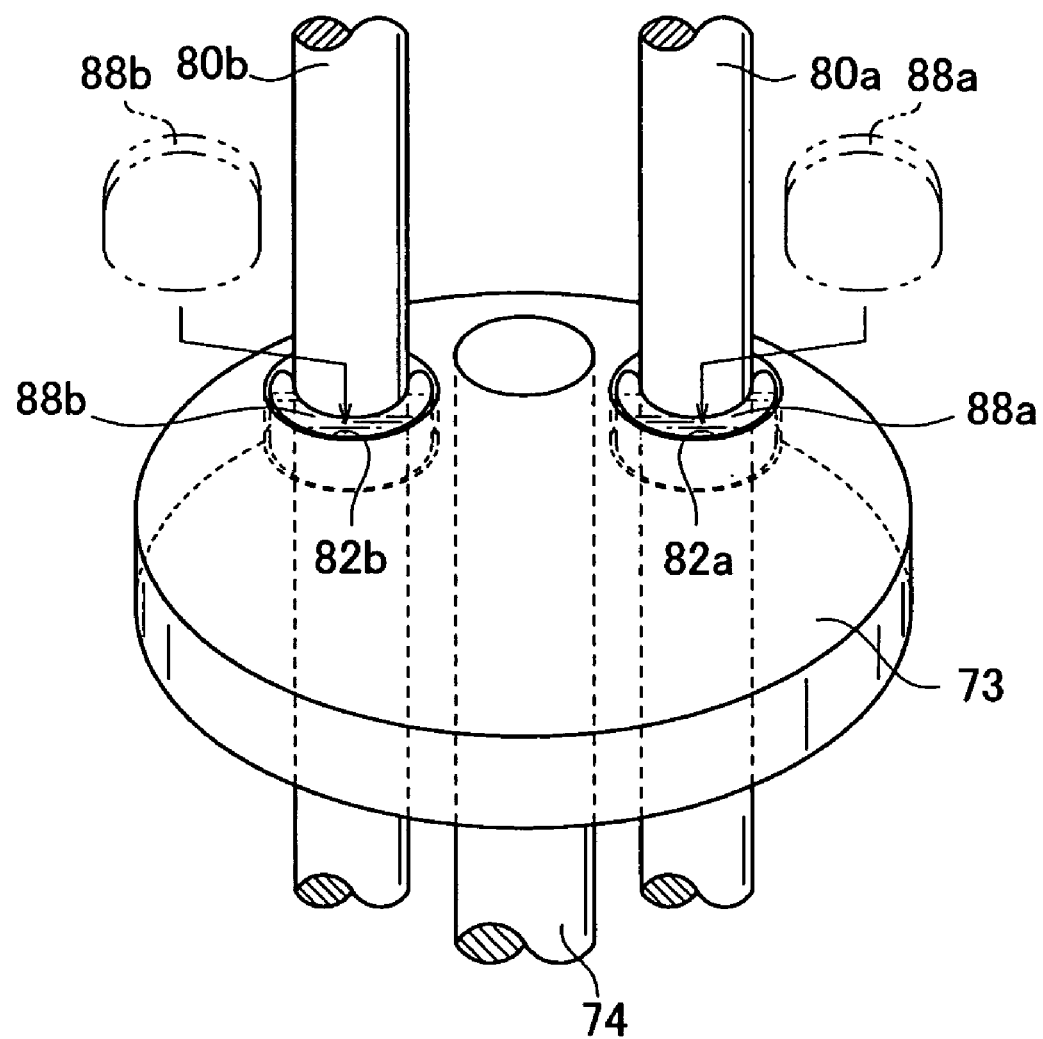
FIG. 8 is a perspective view of shafts and a guide plate in a modified frictional sliding region of the radioactive sample holder according to the first embodiment.

As shown in FIGS. 7 and 8, the second shafts 80a, 80b, to which the syringe holder base 100 engaged by the flange 32 of the syringe 24, are retained on the guide plate 73 under frictional resistance posed by the resistive members 86a, 86b or 88a, 88b. Therefore, when the radiation shield case 40 with the syringe 24 mounted therein is placed on the radioactive sample holder 62, the syringe holder base 100 is prevented from being lowered by gravitational force, and hence the syringe 24 is prevented from being pulled out of the radiation shield case 40.

After the radiation shield case 40 with the syringe 24 mounted therein is held by the radioactive sample holder 62, the operator grips the knob 71 and removes the radioactive sample holder 62 from the mounts 64a, 64b. Then, the operator inserts the radioactive sample holder 62 downwardly into the hollow cylindrical body 60 with the guide plate 76 entering the hollow cylindrical body 60 first. When the radioactive sample holder 62 is inserted in the hollow cylindrical body 60, the guide plate 73 engages in the upper opening of the hollow cylindrical body 60, and the radiation shield plate 72 is disposed on the upper end of the hollow cylindrical body 60. Therefore, external radiations are prevented from entering the hollow cylindrical body 60 while radiations are prevented from leaking out of the radioactive sample measuring apparatus 28.

Figure 9:
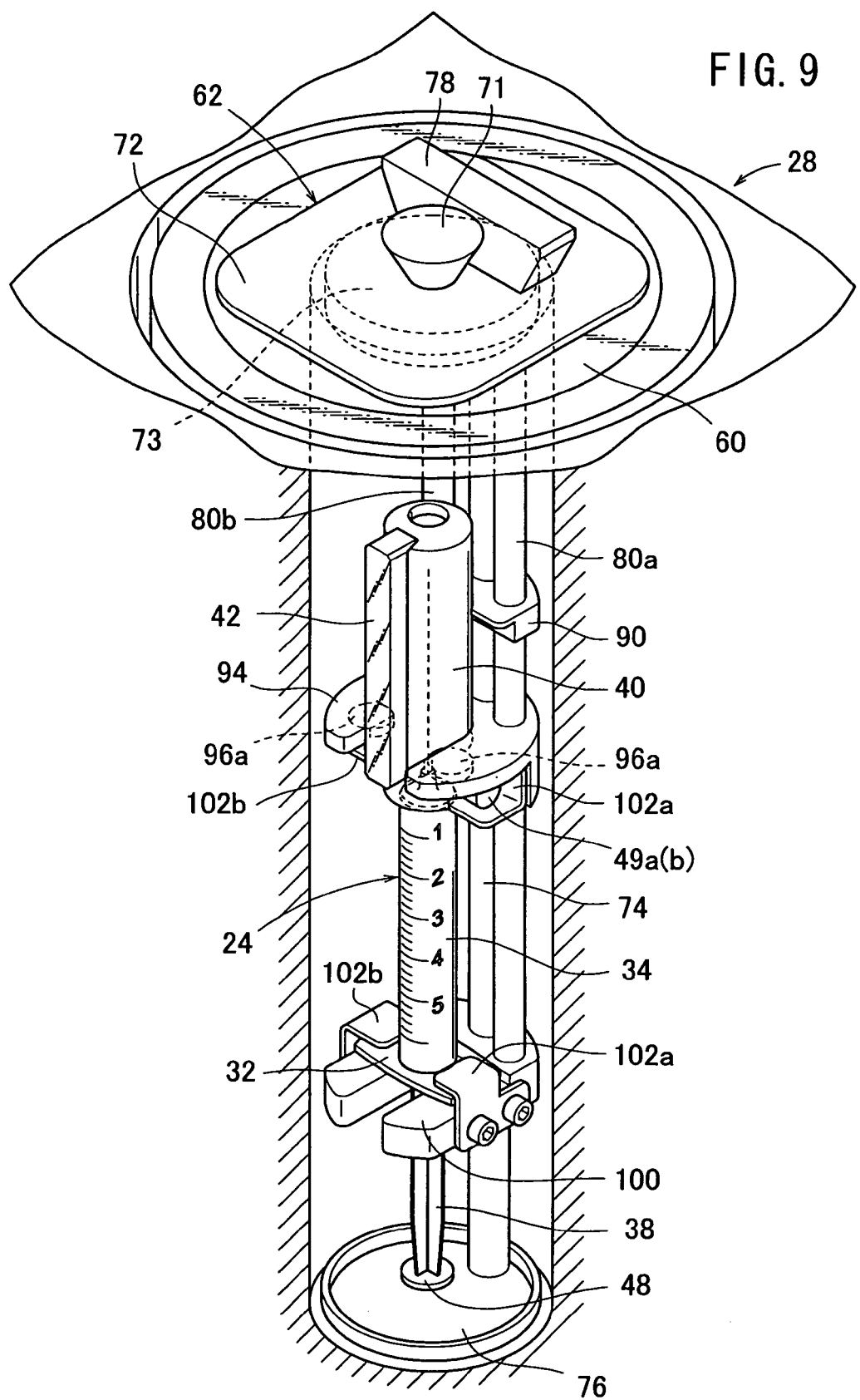
FIG. 9 is a perspective view showing the manner in which the radioactive sample holder according to the first embodiment with the syringe held thereby is inserted into the radioactivity measuring apparatus and an amount of radioactivity of a radioactive sample that is contained in the syringe is measured by the radioactivity measuring apparatus.

Then, the operator depresses the handle 78 of the radioactive sample holder 62. The syringe holder base 100 that is coupled to the handle 78 by the second shafts 80*a*, 80*b* is lowered with the brackets 102*a*, 102*b* engaging the flange 32 of the cylinder 34. The cylinder 34 of the syringe 24 is fully pulled out of the radiation shield case 40, and exposed in the hollow cylindrical body 60 of the radioactive sample measuring apparatus 28 (see FIG. 9).

The operator slides the lead shield plate 54 that is disposed in the lower end of the column 44 into the position above the radioactive sample measuring apparatus 28, preventing external radiations, e.g., radiations from the remaining radioactive sample in the sample container 52, from entering the radioactive sample measuring apparatus 28. Thereafter, the amount of radioactivity of the radioactive sample contained in the syringe 24 is measured under the control of the measurement display unit 30. Since the syringe 24 is fully pulled out of the radiation shield case 40 in the radioactive sample measuring apparatus 28, the amount of radioactivity of the radioactive sample contained in the syringe 24 is measured highly accurately.

After the amount of radioactivity of the radioactive sample is measured, the operator slides the lead shield plate 54 back into the lower end of the column 44, and then lifts the handle 78. The syringe 24 is placed back into the radiation shield case 40 as the syringe holder base 100 is elevated. The tapered surface 47 defined on the annular edge of the radiation shield case 40 that surrounds the lower opening 45 allows the syringe 24 to be reliably and smoothly placed into the radiation shield case 40.

After the syringe 24 is housed in the radiation shield case 40, the operator pulls the radioactive sample holder 62 upwardly from the radioactive sample measuring apparatus 28. The process of introducing and measuring a radioactive sample using the radioactive sample introducing and measuring system 20 is now put to an end.

In the above illustrated embodiment, the syringe holder base 100 is lowered to pull the syringe 24 out of the radiation shield case 40 in the radioactive sample measuring apparatus 28. Alternatively, however, the syringe holder base 100 may be fixed in position, and the radiation shield case 40 may be lifted by the second retainer 94 to expose the syringe 24 in the hollow cylindrical body 60. The radioactive sample measuring apparatus 28, which is illustrated as being integrally combined with the radioactive sample introducing apparatus 26 in the above embodiment, may be separate from the radioactive sample introducing apparatus 26.

Figure 10:
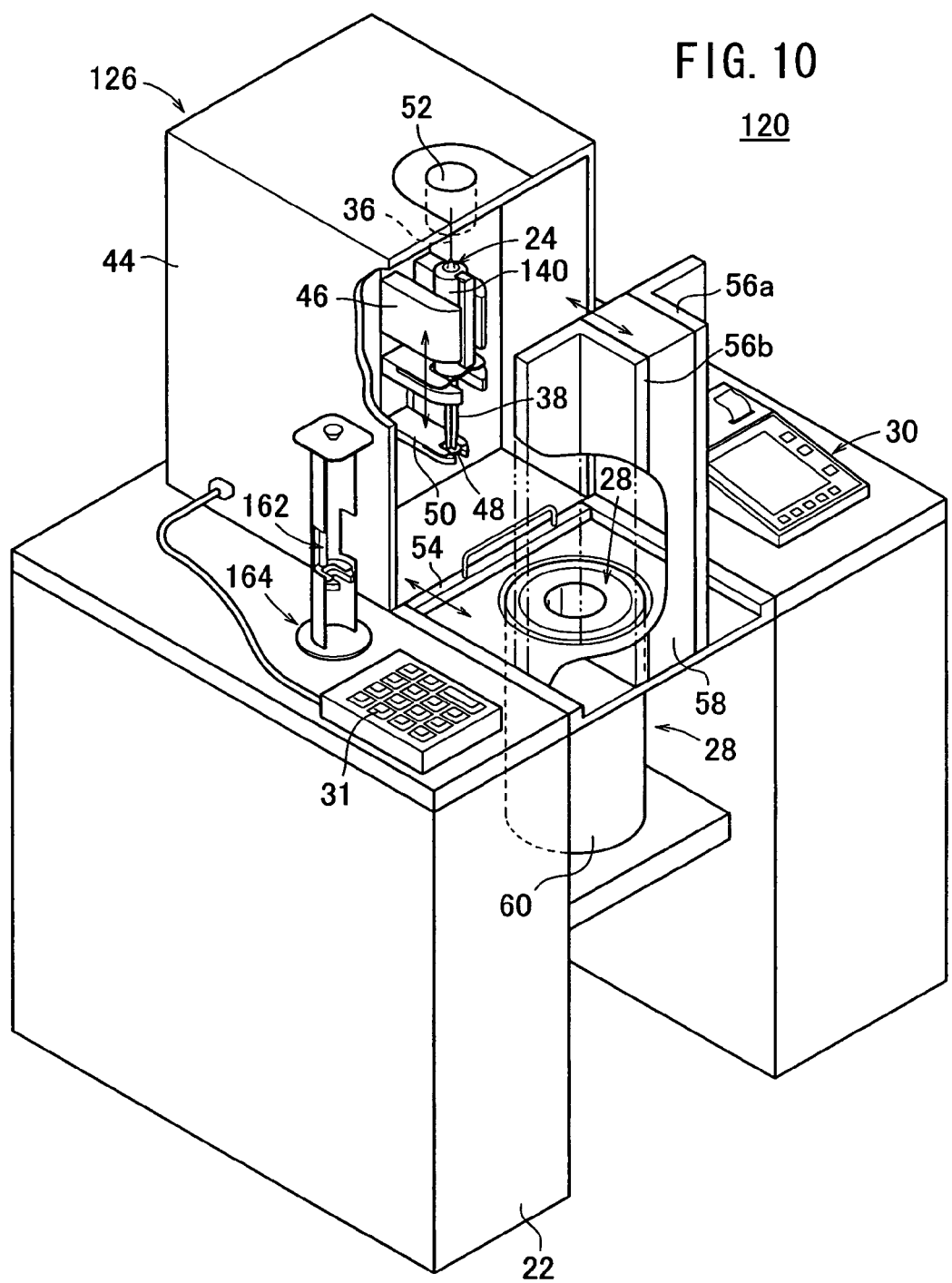
FIG. 10 is a perspective view, partly broken away, of a radioactive sample introducing and measuring system which incorporates a radioactive sample holder according to a second embodiment of the present invention.

FIG. 10 shows in perspective, partly broken away, a radioactive sample introducing and measuring system 120 which incorporates a radioactive sample holder 162 according to a second embodiment of the present invention. Those parts of the radioactive sample introducing and measuring system 120 and the radioactive sample holder 162 which are identical to those of the radioactive sample introducing and measuring system 20 and the radioactive sample holder 62 according to the first embodiment are denoted by identical reference characters, and will not be described in detail below.

Figure 11:
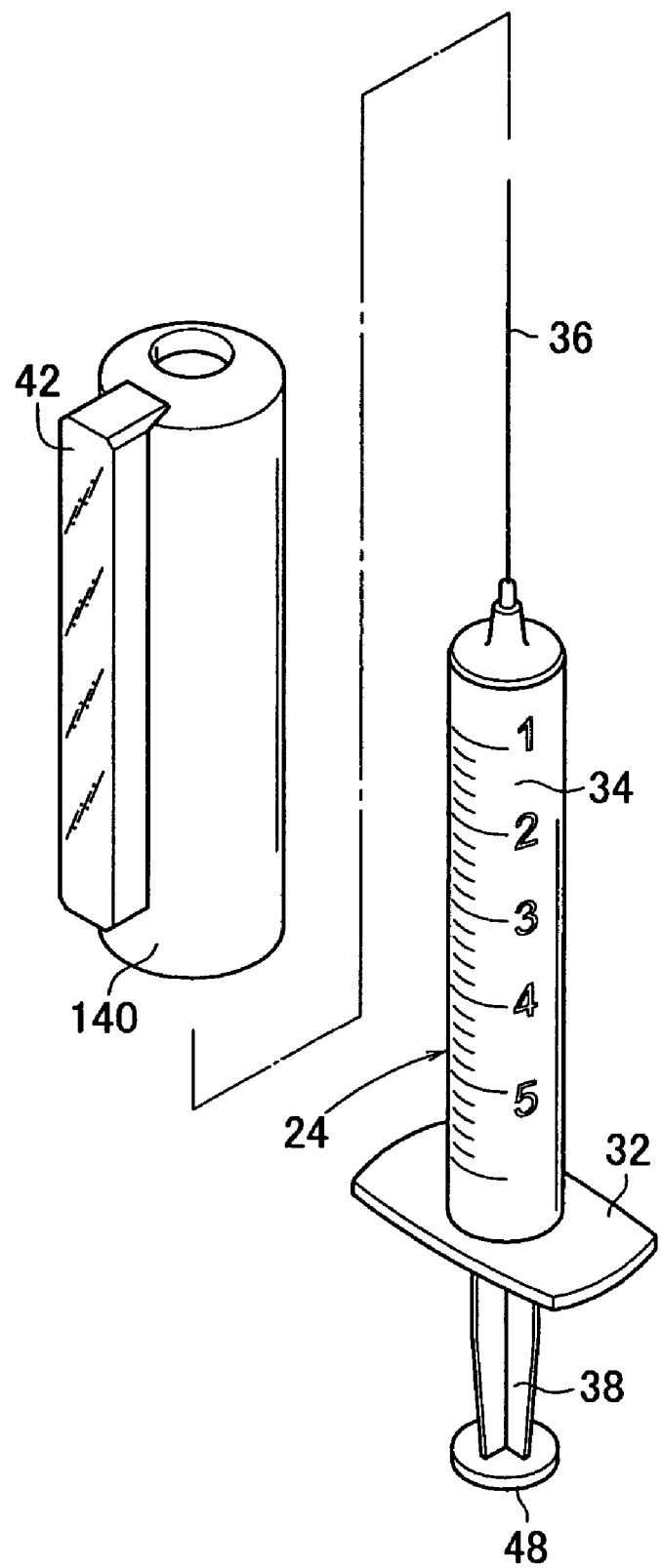
FIG. 11 is a perspective view of a syringe and a radiation shield case which are held by the radioactive sample holder according to the second embodiment.
Figure 12:
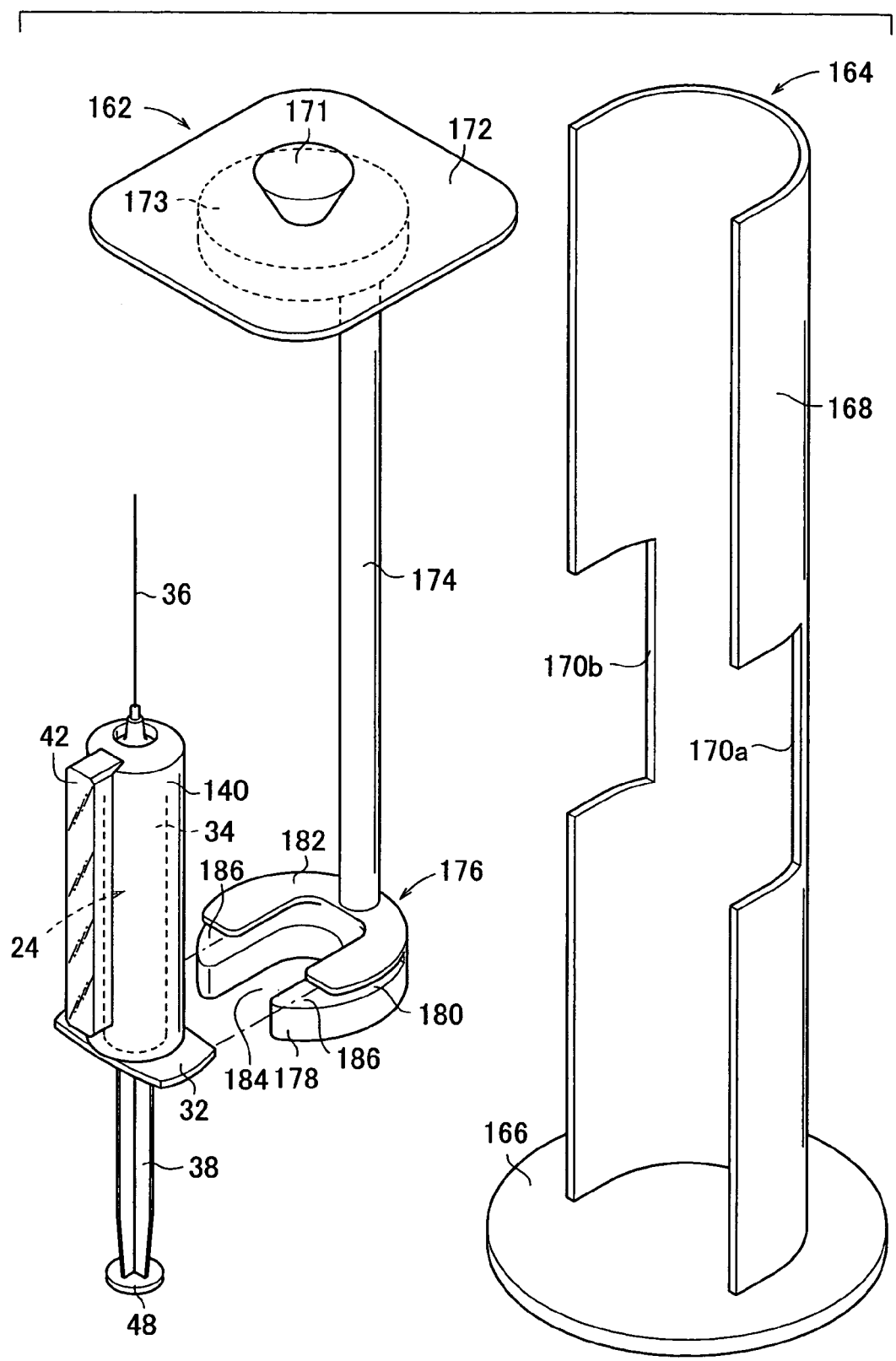
FIG. 12 is an exploded perspective view of the radioactive sample holder according to the second embodiment and a stand for holding the radioactive sample holder.

The radioactive sample introducing and measuring system 120 has a radioactive sample introducing apparatus 126 and a stand 164 for supporting the radioactive sample holder 162 according to the second embodiment, the stand 164 being disposed laterally of the radioactive sample introducing apparatus 126. The radioactive sample holder 162 holds the syringe 24 that is housed in a radiation shield case 140 shown in FIG. 11. As shown in FIG. 12, the stand 164 has a hollow semicylindrical body 168 vertically mounted on a circular support base 166. The hollow semicylindrical body 168 has a pair of diametrically opposite recesses 170*a*, 170*b* defined in a substantially vertically central region thereof.

The radioactive sample holder 162 comprises a radiation shield plate 172 made of a radiation shielding material such as tungsten or the like and having a knob 171 on its upper surface, a circular guide plate 173 mounted on a lower surface of the radiation shield plate 172 and having a diameter substantially equal to the inside diameter of the hollow cylindrical body 60 of the radioactive sample measuring apparatus 28, a shaft 174 extending vertically downwardly from the radiation shield plate 172, and a substantially circular retainer 176 mounted on the lower end of the shaft 174 and having a diameter slightly smaller than the inside diameter of the hollow cylindrical body 60. The retainer 176 serves to hold the syringe 24 inserted in the radiation shield case 140 in a vertical orientation.

The retainer 176 comprises a first support 178 for supporting the lower surface of the flange 32 of the cylinder 34 of the syringe 24, a second support 182 for supporting the upper surface of the flange 32, the second support 182 being disposed above the first support 178 and spaced therefrom by a distance corresponding to the thickness of the flange 32, and a U-shaped groove 184 defined in and between the first support 178 and the second support 182. The first support 178 has a front step 186 projecting a predetermined distance forwardly from the second support 182.

The radioactive sample introducing and measuring system 120 which incorporates the radioactive sample holder 162 according to the second embodiment is basically constructed as described above. A process of introducing and measuring a radioactive sample using the radioactive sample introducing and measuring system 120 will be described below.

After the operator has introduced a radioactive sample into the syringe 24 in the same manner as with the first embodiment, the operator displaces the lead glass plate 58 away from the radioactive sample introducing apparatus 126, and removes the radiation shield case 140 with the syringe 24 mounted therein from the retainer 46. Then, the operator places the radiation shield case 140 with the syringe 24 mounted therein on the radioactive sample holder 162 that is disposed on the stand 164 on the worktable 22.

Figure 13:
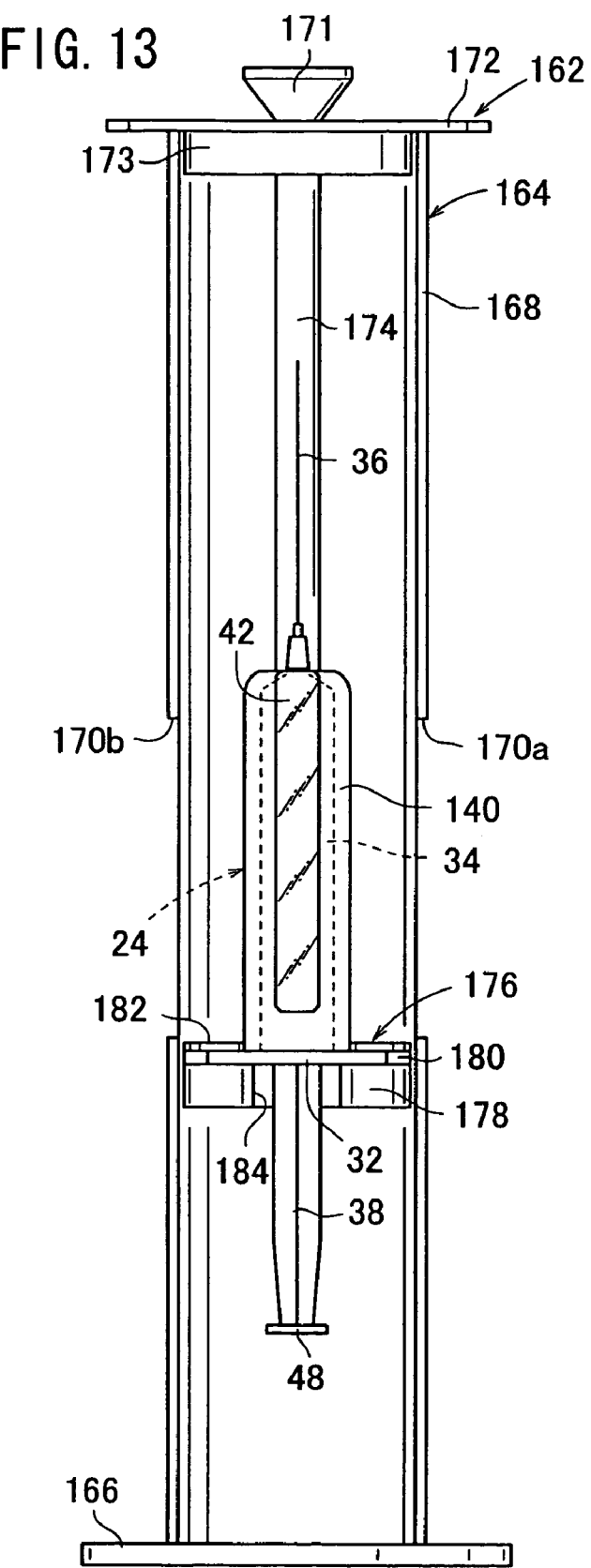
FIG. 13 is a front elevational view showing the syringe which is held by the radioactive sample holder according to the second embodiment through the stand.
Figure 14:
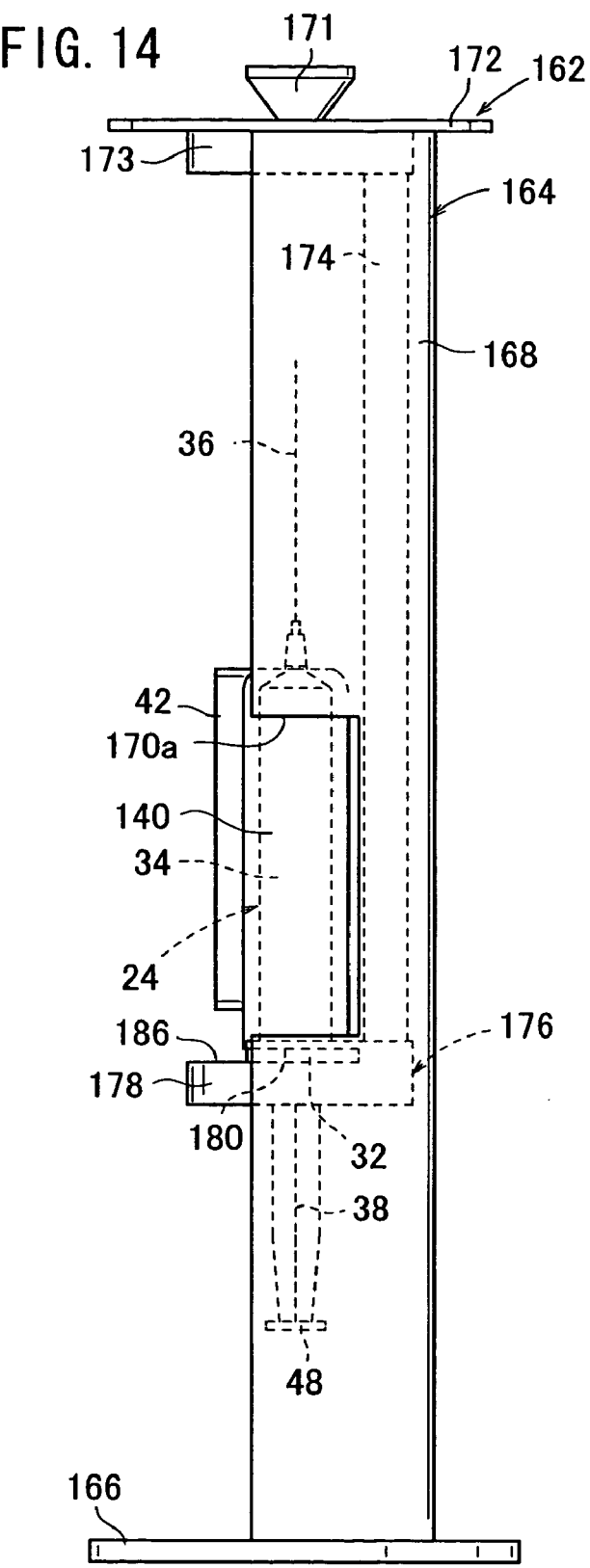
FIG. 14 is a side elevational view showing the syringe which is held by the radioactive sample holder according to the second embodiment through the stand.

At this time, as shown in FIGS. 13 and 14, the radioactive sample holder 162 is in such an operative position that the radiation shield plate 172 is placed on the upper end of the hollow semicylindrical body 168 of the stand 164. The operator inserts the radiation shield case 140 with the syringe 24 mounted therein into the hollow semicylindrical body 168 through its open side with the needle 36 pointing upwardly, thus placing the radiation shield case 140 on the radioactive sample holder 162.

Specifically, the flange 32 of the cylinder 34 is placed on the step 186 of the first support 178 of the retainer 176, and inserted into a gap 180 between the first support 178 and the second support 182, with the piston 38 being inserted into the U-shaped groove 184 defined in and between the first support 178 and the second support 182. Since the syringe 24 is placed on the radioactive sample holder 162 with the needle 36 pointing upwardly, the radioactive sample contained in the cylinder 34 does not leak out accidentally.

Because of the recesses 170a, 170b of the stand 164, the hollow semicylindrical body 168 does not obstruct the operator's action to place the radiation shield case 140 with the syringe 24 mounted therein on the retainer 176. Therefore, the operator finds it easy to set the syringe 24 on the stand 164.

When the radiation shield case 140 with the syringe 24 mounted therein is placed on the radioactive sample holder 162, the flange 32 of the cylinder 34 is vertically held between the first support 178 and the second support 182, and the weight of the radiation shield case 140 that is made of a heavy metal acts on the flange 32. Therefore, the syringe 24 with the needle 36 pointing upwardly is firmly held by the radioactive sample holder 162. Furthermore, inasmuch as the radioactive sample holder 162 is retained by the stand 164, the operator can place the radiation shield case 140 with the syringe 24 mounted therein easily on the radioactive sample holder 162 without manually holding the radioactive sample holder 162.

The radioactive sample holder 162 is arranged to hold the syringe 24 with the flange 32 of the cylinder 34 inserted in the gap 180 between the first support 178 and the second support 182. Therefore, the radioactive sample holder 162 is able to hold various syringes 24 of different sizes insofar as their pistons 38 have diameters small enough to be inserted into the U-shaped groove 184.

Figure 15:
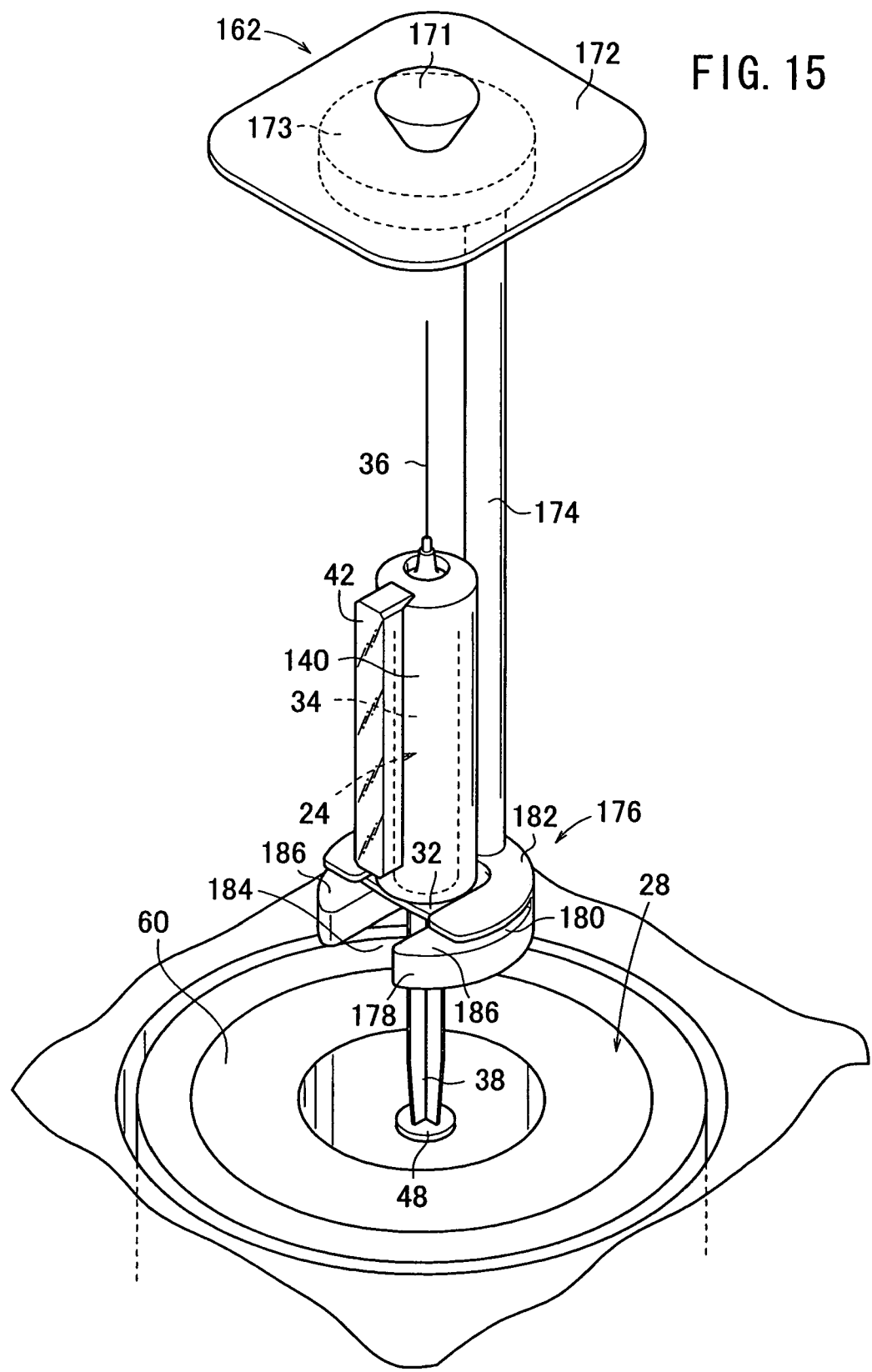
FIG. 15 is a perspective view showing the manner in which the radioactive sample holder according to the second embodiment with the syringe held thereby is inserted into a radioactivity detector.
Figure 16:
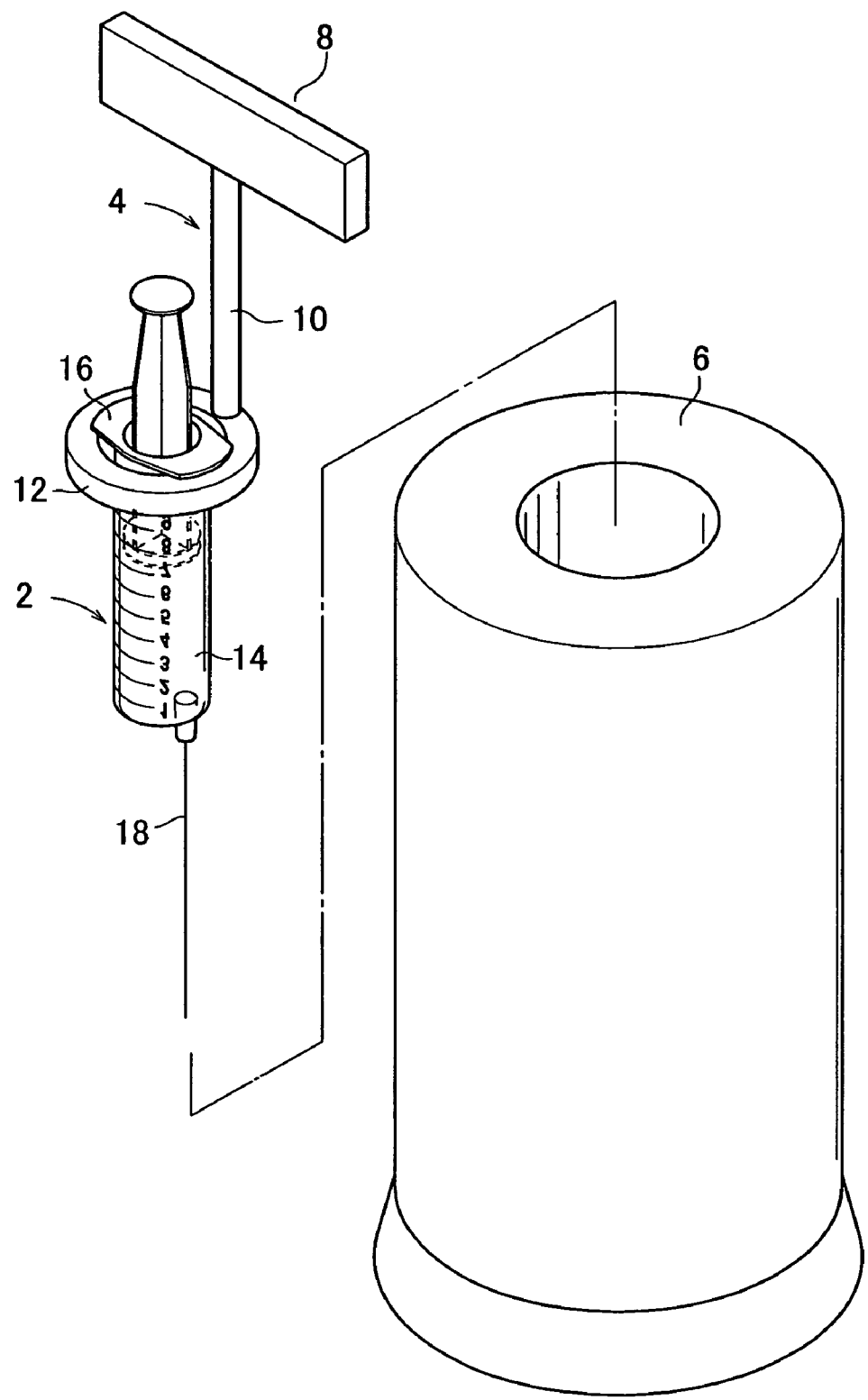
FIG. 16 is a perspective view of a conventional radioactive sample holder.

After the radiation shield case 140 with the syringe 24 mounted therein is held by the radioactive sample holder 162, the operator grips the knob 171 and removes the radioactive sample holder 162 with the syringe 24 from the stand 164. Then, the operator inserts the radioactive sample holder 162 downwardly into the hollow cylindrical body 60 of the radioactive sample measuring apparatus 28 with the retainer 176 entering the hollow cylindrical body 60 first (see FIG. 15). When the radioactive sample holder 162 is inserted in the hollow cylindrical body 60, the guide plate 173 engages in the upper opening of the hollow cylindrical body 60, and the radiation shield plate 172 is disposed on the upper end of the hollow cylindrical body 60. Therefore, external radiations are prevented from entering the hollow cylindrical body 60, and radiations are prevented from leaking out of the radioactive sample measuring apparatus 28.

Then, the operator slides the lead shield plate 54 that is disposed in the lower end of the column 44 into the position above the radioactive sample measuring apparatus 28. Thereafter, the amount of radioactivity of the radioactive sample contained in the syringe 24 is measured for under the control of the measurement display unit 30.

When the amount of radioactivity is measured, since the radiation shield case 140 is mounted on the syringe 24, the measured amount of radioactivity of the radioactive sample contained in the syringe 24 is smaller than the actual amount of radioactivity of the radioactive sample contained in the syringe 24. However, the amount of radioactivity of the radioactive sample contained in the syringe 24 can accurately be estimated by correcting the measured value based on a corrective table of values that have directly been measured from radioactive samples contained in the syringe 24 not covered with the radiation shield case 140.

Although certain preferred embodiments of the present invention have been shown and described in detail, it should be understood that various changes and modifications may be made therein without departing from the scope of the appended claims.

What is claimed is:

1. A radioactive sample holder for holding a syringe containing a radioactive sample therein, the radioactive sample holder being adapted to be loaded into a radioactivity measuring apparatus for measuring an amount of radioactivity of the radioactive sample, comprising:
   a radiation shield plate;
   a shaft extending vertically downwardly from said radiation shield plate; and
   a retainer disposed on a lower end portion of said shaft, for vertically retaining said syringe;
   said retainer having a first support for supporting a lower surface of a flange of a cylinder of said syringe, a second support disposed above said first support at a spaced interval therefrom, for supporting an upper surface of said flange, and a groove defined in said first support and said second support, for inserting a piston of said syringe horizontally therein.

2. A radioactive sample holder according to claim 1, wherein said first support projects a predetermined distance horizontally from said second support.

3. A radioactive sample holder according to claim 1, wherein said syringe has a needle and is retained by said retainer with said needle pointing upwardly.

4. A radioactive sample holder according to claim 1, further comprising a radiation shield case for housing said cylinder therein, wherein said syringe is retained by said retainer with said cylinder housed in said radiation shield case.

5. A radioactive sample holder according to claim 4, wherein said retainer has a third support for supporting said radiation shield case; and
   said shaft comprises a first shaft and a second shaft, said third support being mounted on said first shaft, and said first support and said second support being mounted on said second shaft;
   said radioactive sample holder further comprising:
   a handle coupled to an upper end of said first shaft or said second shaft above said radiation shield plate, for vertically displacing said first shaft or said second shaft through said radiation shield plate, said handle being operable to take said syringe into and out of said radiation shield case.

6. A radioactive sample holder according to claim 5, wherein said third support comprises a first retainer for holding an upper outer circumferential surface of said radiation shield case, a second retainer for holding a lower outer circumferential surface of said radiation shield case, and a third retainer for holding an arm projecting from a side surface of said radiation shield case.

7. A radioactive sample holder according to claim 6, wherein said second retainer has a resistive member for engaging said radiation shield case to impart frictional resistance to said radiation shield case.

8. A radioactive sample holder according to claim 5, further comprising a resistive member for imparting frictional resistance to said first shaft or said second shaft, said resistive member being disposed in a frictional sliding region between said radiation shield plate and said first shaft or said second shaft which is vertically displaceable with respect to said radiation shield plate.

* * * * *